United States Patent [19]
Delhaye et al.

[11] Patent Number: 5,424,825
[45] Date of Patent: Jun. 13, 1995

[54] SPECTRAL-BAND FILTRATION SPECTROMETRY APPARATUS

[75] Inventors: Michel Delhaye, Villeneuve d'Ascq; Edouard Da Silva, Lille; Gérard Martinez, Fontaine, all of France

[73] Assignee: Dilor, Lille, France

[21] Appl. No.: 953,887

[22] Filed: Sep. 30, 1992

[30] Foreign Application Priority Data

Oct. 1, 1991 [FR] France ............................ 92 11061

[51] Int. Cl.⁶ .......................... G01J 3/30; G01J 3/44
[52] U.S. Cl. ..................................... 356/318; 356/301
[58] Field of Search ................. 356/318, 417, 301

[56] References Cited

U.S. PATENT DOCUMENTS

| | | |
|---|---|---|
| 3,554,647 | 1/1971 | Paine . |
| 3,865,490 | 2/1975 | Grossman ........................ 356/301 |
| 3,907,430 | 9/1975 | Mann . |
| 4,025,196 | 5/1977 | Chupp et al. . |
| 4,235,518 | 11/1980 | Greiner . |

FOREIGN PATENT DOCUMENTS

| | | |
|---|---|---|
| 0184428 | 11/1986 | European Pat. Off. . |
| 0010834 | 1/1984 | Japan ................................ 356/301 |

OTHER PUBLICATIONS

Premonochromator for Stray Light Rejection in Raman Spectroscopy, J. Fellman et al., *Applied Optics*, vol. 16, No. 4, Apr. 1, 1977, pp. 1085-1087.
Un Triple Monochromateur Pour La Spectroscopie Raman A Basses Frequences, C. Julien, *Journal of Optics*, vol. 11, No. 4, Aug. 1, 1980, pp. 257-267.

*Primary Examiner*—Vincent P. McGraw
*Assistant Examiner*—K. P. Hantis
*Attorney, Agent, or Firm*—Dennison, Meserole, Pollack & Scheiner

[57] ABSTRACT

The filtration means filter the exciter radiation (EX) in a first forward direction from generator means (LS) to the specimen (EC), by allowing a second spectral band (BZ) of predetermined spectral width (l) and centered on a selected frequency corresponding to the wavelength of the exciter radiation (L0) to pass and stopping a first spectral band (FZ) complementary to the second spectral band (BZ), while substantially simultaneously with this first filtration operation, these filtration means further filter the analysis radiation (ON) in a second direction that is the reverse of the first direction, by allowing the first spectral band (FZ) to pass and stopping the second spectral band (BZ).

9 Claims, 12 Drawing Sheets

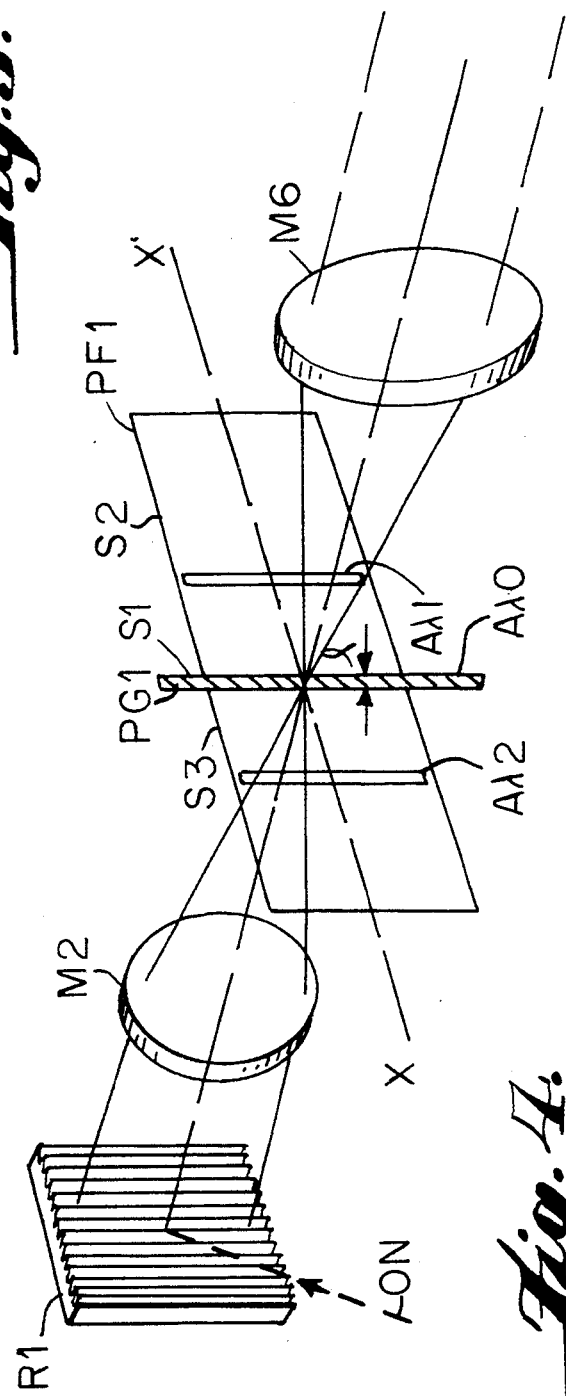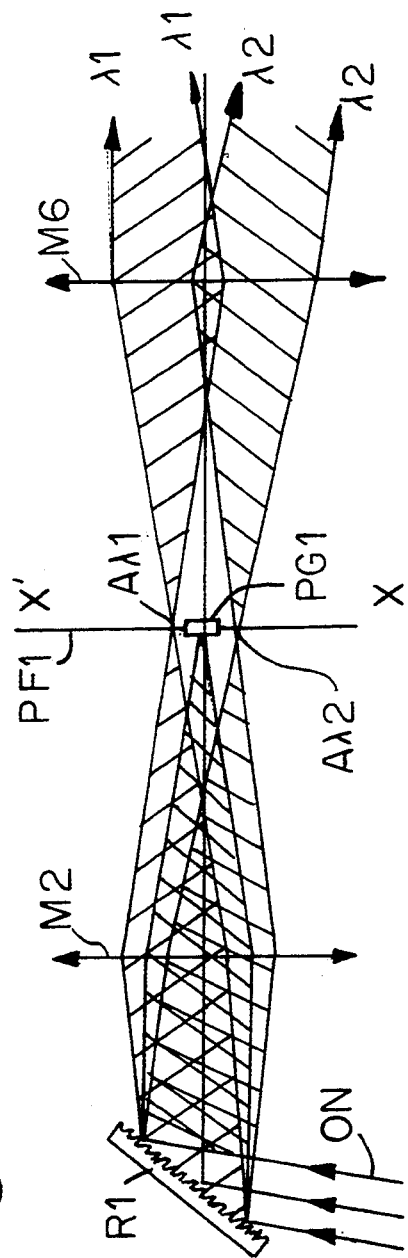

1

SPECTRAL-BAND FILTRATION SPECTROMETRY APPARATUS

BACKGROUND OF THE INVENTION

The invention relates to spectral-band filtration spectrometry.

It is used in spectrochemical analysis that works by emission, luminescence, phosphorescence, Raman scattering, etc.

Spectral-band filtration spectrometry apparatuses are already known.

Such apparatuses generally include the following:

generator means arranged to generate an exciter electromagnetic radiation of a predetermined wavelength;

a specimen to be analyzed;

an input for an electromagnetic radiation beam for characteristic analysis of the specimen; and optical means arranged to carry the exciter electromagnetic radiation to the specimen, to receive the resultant analysis beam originating in the thus-excited specimen, limited to a selected spectral band.

Numerous optical filtration means exist that perform the filtration in a narrow spectral band or ray.

SUMMARY OF THE INVENTION

The present applicant faced the problem of innovation in such a way as to use such filtration means in order to improve their filtration properties in a spectrometry apparatus.

Hence a first object of the invention is to achieve optical filtration means capable of simultaneously assuring the rejection of a narrow spectral band, and the injection in the opposite direction of radiation with a wavelength centered on this same central band.

A second object of the invention is to achieve filtration means having a very steep slope of attenuation in the vicinity of the wavelength to be filtered.

A third object of the invention is to furnish filtration means that are removable and are adjustable around any wavelength to be filtered.

The invention relates to a dispersive spectrometry apparatus of the known type.

Such a structure is of major interest.

In fact, it is highly advantageous, for example when the light source employed emits not only useful radiation but other radiations as well, having wavelengths that differ from that of the useful radiation and are considered undesirable. This is true particularly for variable-mode diode lasers, dye lasers, or lasers emitting both intense stimulated radiation and nonstimulated rays due to the plasma or pump sources.

Such a structure also has the advantage of dispensing with the optical elements typically used in a spectrometry apparatus, such as the dichroic plates separating beams. In addition, it is easy to use.

In practice, the filtration means perform filtering by reflection, transmission, or refraction.

Further advantages and characteristics of the invention will become apparent from the ensuing description and the accompanying drawings:

BRIEF DESCRIPTION OF DRAWINGS

FIG. 3 is a more detailed view of the light trap of FIG. 2;

FIG. 4 is a sectional view taken along the line XX' through the light trap of FIG. 3;

DESCRIPTION OF INVENTION

The drawings essentially include elements of a certain nature. They are accordingly an integral portion of the description and can serve not only to provide better comprehension of the detailed description but also to contribute as applicable to the definition of the invention.

Figure 1:
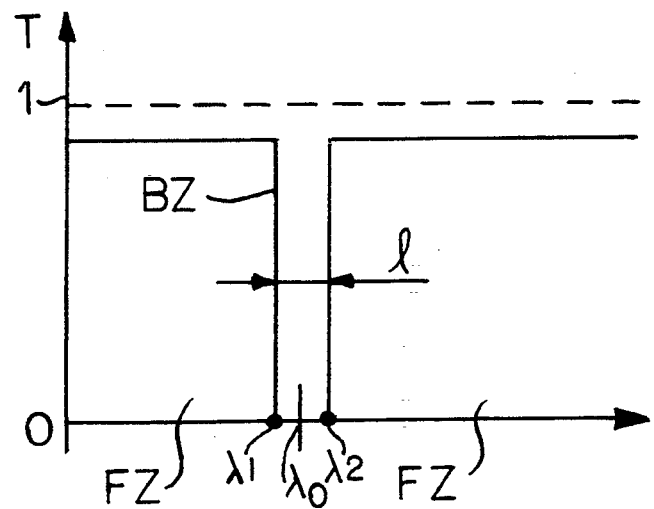
FIG. 1 shows the spectral response of an ideal filter of the band eliminating type.

In FIG. 1, a curve has been shown, illustrating the spectral response of an ideal optical filter of the band-eliminating or band-rejection type.

The transmittance T of the filter is plotted on the ordinate and the frequency or wavelength λ of the electromagnetic radiation to be filtered is plotted on the abscissa.

The spectral response of an ideal band-eliminating or band-rejector filter has a rectangular profile. It allows the radiation having a wavelength less than a wavelength λ1 and greater than a wavelength λ2 to pass with a maximum transmission value, and it eliminates, with a zero transmission value, the radiation having a wavelength between λ1 and λ2, or in other words radiation centered around the central frequency λ0.

In practice, the special band BZ eliminated or rejected has a width 1 proportional to the difference λ2−λ1. The remainder of the spectrum forms the passband FZ.

Figure 2:
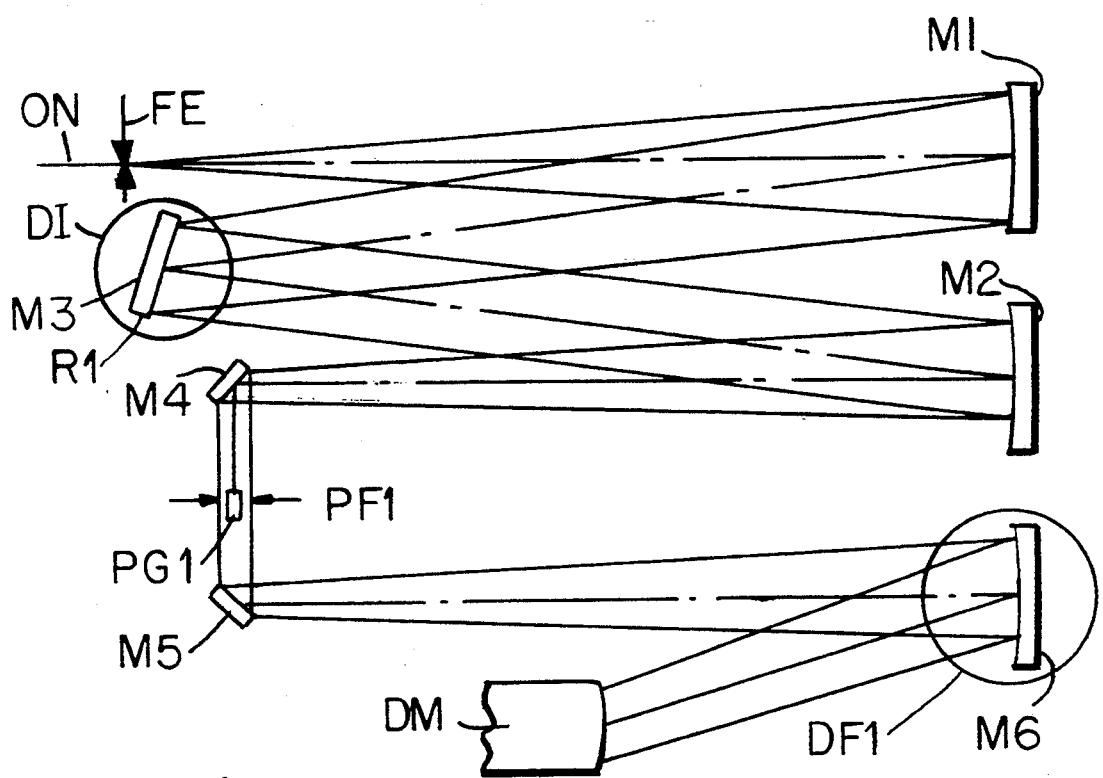
FIG. 2 is a schematic view of an apparatus with a dispersive state equipped with an absorption-type light trap.

In FIG. 2, a dispersive spectrometry installation has been shown.

A lens (not shown) focuses the electromagnetic radiation ON to be analyzed onto an inlet slit FE.

The inlet beam is received by a dispersive stage DI, for example including a disperser network R1 disposed between two mirrors M1 and M2.

In practice, a mirror M3 may be mounted on the back of the network R1, which is carried by a mechanism (not shown) enabling a controlled rotation around an axis perpendicular to the plane of FIG. 2.

A mirror M2 focuses the dispersed spectral image onto filtration means that form a light trap PG1 in accordance with an optical property included in the group comprising absorption, transmission, reflection and refraction. The dispersed spectral image is focused onto PG1 here via reflection at a plane mirror M4.

The light trap PG1 is placed at the level of the focal plane PF1 of the mirror M2 in order, by the aforementioned optical property, to trap a spectral band BZ having a predetermined spectral width 1 and centered on a selected frequency corresponding to the wavelength λ0 of the electromagnetic radiation to be trapped, while authorizing processing of the dispersed spectral image without this thus-trapped spectral band in a detection module DM.

In practice, the dispersed spectral image FZ, minus the spectral band BZ thus trapped, is transmitted to a detection module DM either directly or a deflector stage DF.

The deflector stage DF, which for example includes mirrors M5 and M6, then precedes the detection module DM.

In FIGS. 3 and 4, means forming an absorption-type light trap have been shown in further detail.

The network R1 is seen here, which disperses the beam ON to be analyzed.

An objective, constituted by a lens or spherical mirror M2, forms the spectral image dispersed by the dispersive stage R1 in a focal plane PF1 for a selected frequency corresponding to the wavelength λ0.

Filtration means forming an absorption-type light trap PG1, which will be described in further detail hereinafter, are placed at the level of the focal plane PF1.

For the sake of better comprehension of the description, the points Aλ2, Aλ0, and Aλ1 represent the intersections of the dispersed spectral image formed by the mirror M2 with the focal plane PF1, for the respective wavelengths λ2, λ0 and λ1.

It should be noted that the intersections for λ1 and λ2 are disposed on either side of the one for λ0.

In FIGS. 2, 3 and 4, the means forming the light trap PG1 are of the absorption light trap type; that is, they include a surface S1 constituted by an absorbent material and having a predetermined absorbent width capable of absorbing a spectral band BZ of predetermined spectral width 1 and centered on the selected frequency corresponding to the wavelength λ0 of the electromagnetic radiation to be trapped.

The absorbent surface S1 is interposed between transparent surfaces S2 and S3, to allow the dispersed spectral image FZ, minus the spectral band BZ thus trapped, to pass through for the sake of a later analysis.

As will be seen in further detail hereinafter, it is possible to modify the form of the means embodying an absorption-type light trap, in order to adapt them to the curvature of the spectral rays to be eliminated.

For example, in terms of form, the means embodying an absorption-type light trap has rectilinear or curvilinear edges.

Figure 5:
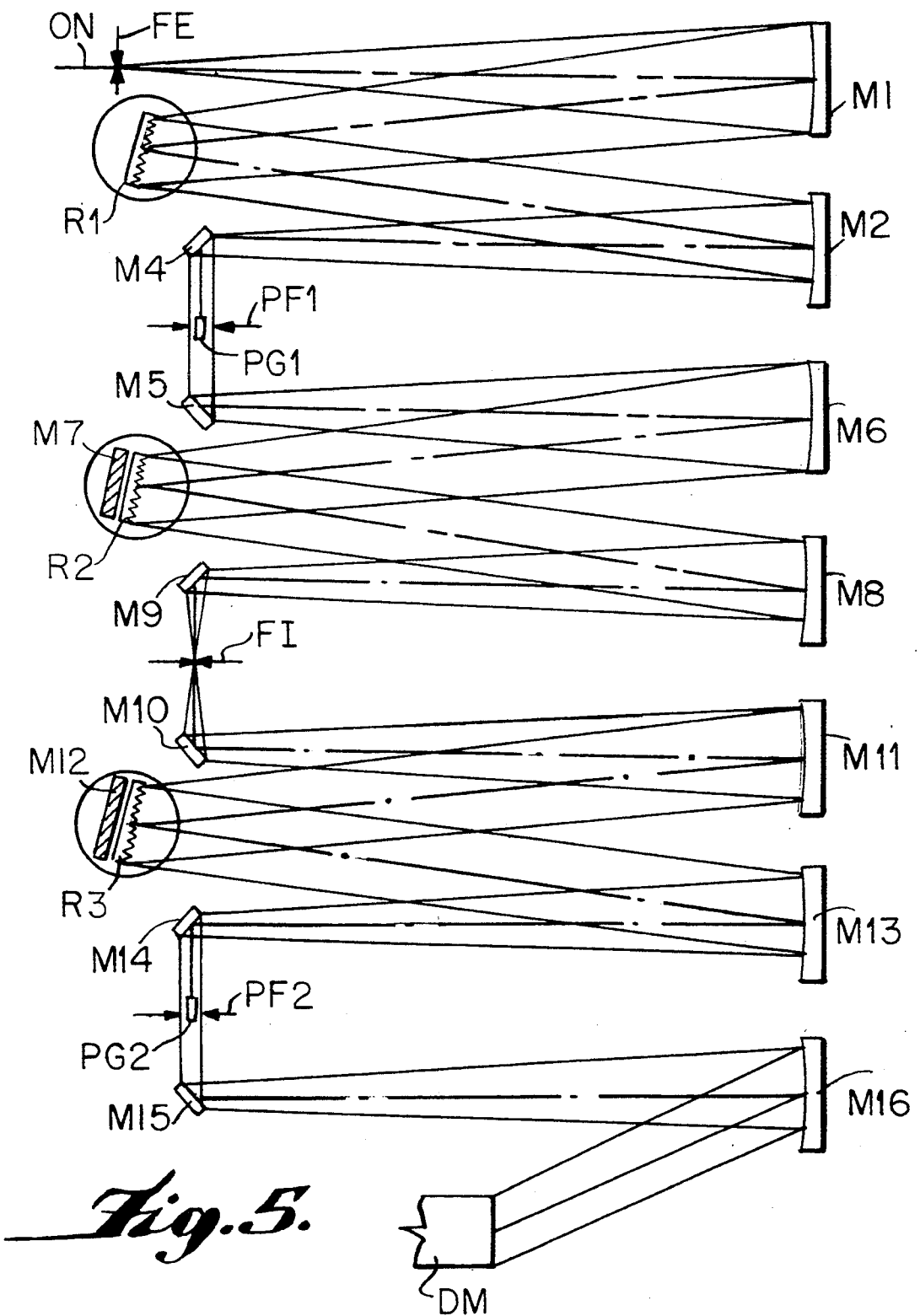
FIG. 5 is a schematic view of an apparatus with multiple dispersive stages each equipped with a light trap.

FIG. 5 shows a dispersive spectrometry installation with a plurality of dispersive stages.

A first dispersive stage is seen initially, including the elements FE through M6, which are identical to those described in conjunction with FIG. 2.

The concave mirror M6 receives the dispersed spectral image FZ minus the spectral band BZ and reforms parallel beams at a second dispersive stage or network R2, whose dispersion is selected to compensate for the dispersion of the first network or stage R1.

A concave mirror M8 receiving the radiation at various wavelengths, thus recombined by the network R2, focuses these radiations onto an intermediate slit FI after reflection at a plane mirror M9.

In practice, the width of the intermediate slit FI is selected to be equal to that of the inlet slit FE. The width of the total spectral band transmitted is adjusted as a function of the focal plane PF1, while the width of the rejected spectral band, centered on λ0, is adjusted as a function of the width of the means forming the light trap PG1.

The thus-filtered radiation is transmitted, via the plane mirror M10, to a third disperser stage DF.

The disperser stage DF includes a disperser network R3, for example, disposed between two spherical mirrors M11 and M13. In practice, a mirror M12 may be mounted on the back of the network R3.

A mirror M14 sends the dispersed spectral image, which originated in the mirror M13, to filtration means that form a second light trap PG2 operating by an optical property included in the group comprising absorption, transmission, reflection and refraction.

The light trap PG2 is placed at the level of the focal plane PF2 of the mirror M13, in order by this optical property to trap a spectral band BZ centered on λ0.

Next, the dispersed spectral image is transmitted to a deflector stage DF2 via a mirror M15.

The deflector stage DF2, which for example includes a mirror M16, precedes a detection module DM.

Advantageously, the inlet slit FE, the focal plane PF1, the intermediate slit FI, and the focal plane PF2 are optically conjugated with one another, to reduce the light diffused by the dispersive stages R1, R2 and R3.

Such a structure accordingly makes it possible to improve the contrast and the rejection of the light diffused by the dispersive and deflector stages.

This kind of advantage thus makes it possible to considerably reduce the transmission of the diffused light at the wavelength λ0 by all the optical elements of the dispersive spectrometry apparatus.

It should be noted that the installation lends itself well to the interposition of filtration means forming a light trap at the output of the mirror M13, that is, for the dispersed spectral image intended to be projected onto a detection module DM.

In a variant, the light trap means PG2 may be followed by a repeater or variable-enlargement optical element (not shown) interposed between the focal plane PF2 and the detection module DM.

Figure 6:
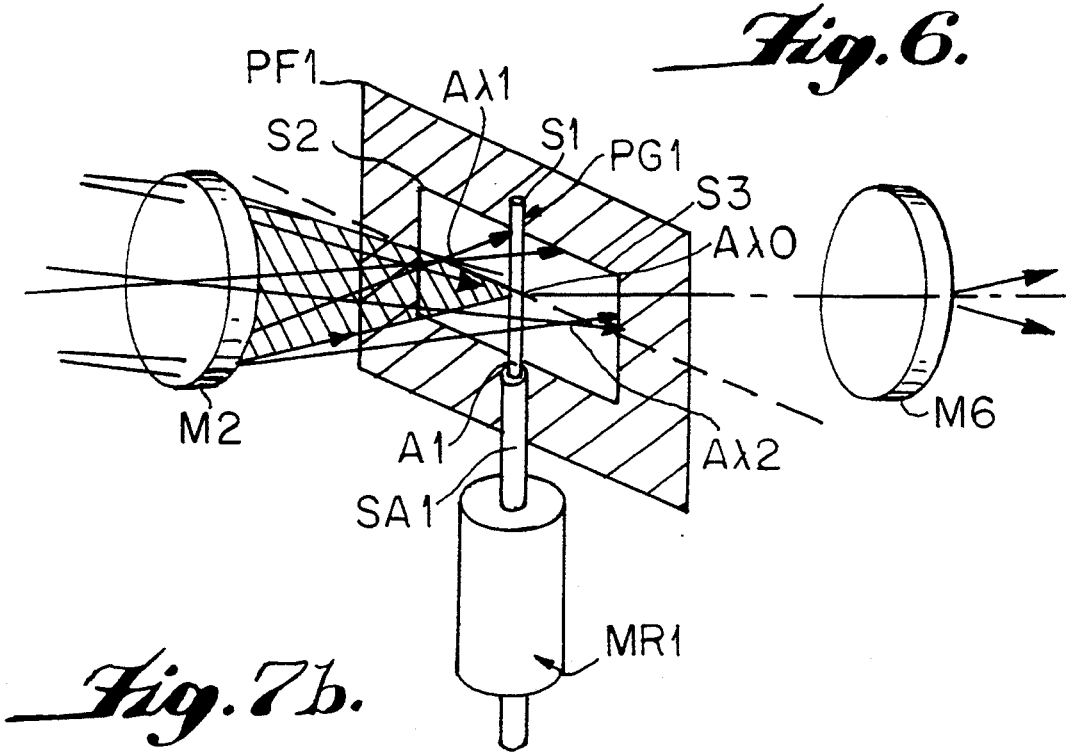
FIG. 6 is a schematic view of a needle forming an absorption-type light trap.

Reference will now be made to FIG. 6, which shows an embodiment of the means forming a light trap by absorption.

This figure shows the means M4 capable of transferring the spectral image dispersed by the dispersive stage R1 to a focal plane PF1, for a selected spectral band centered around $\lambda 0$.

The absorption-light trap PG1 includes a needle A1 of cylindrical cross section S1 cut longitudinally.

In practice, the hollow portion of the semicylindrical cross section S1 of the needle A1 is opaque and has a predetermined width.

Advantageously, the needle is mounted on a needle support SA1 arranged to be movable in a three-dimensional reference system.

For example, the support SA1 is moved by a positioning system MR1.

This kind of mounting enables easy extension and retraction of the light trap PG1 as well as its adjustment in a three-dimensional reference system.

Figure 7B:
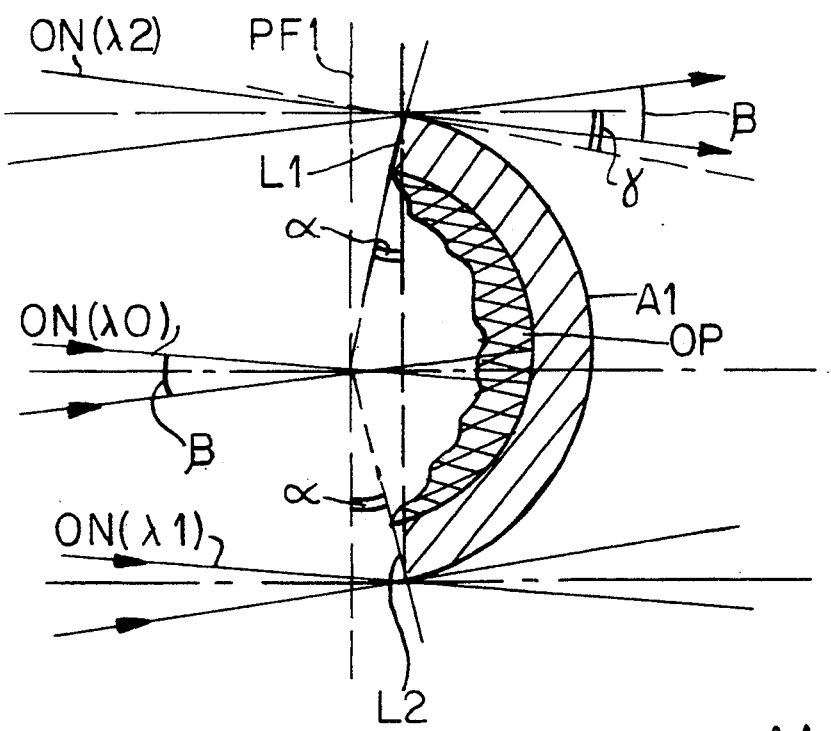
FIGS. 7A and 7B schematically show a tubular needle.
Figure 7A:
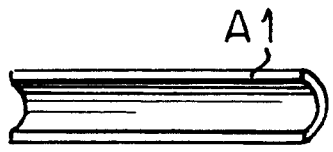

In FIG. 7A, the semicylindrical cross section of the needle A1 is shown in detail. The diameter of the needle defines the width of the light trap.

In FIG. 7B, the hollow part of the semicylindrical section of the needle A is covered with an opaque material OP capable of absorbing the luminous radiation for a predetermined frequency.

The material OP is black paint, for example.

Figure 8:
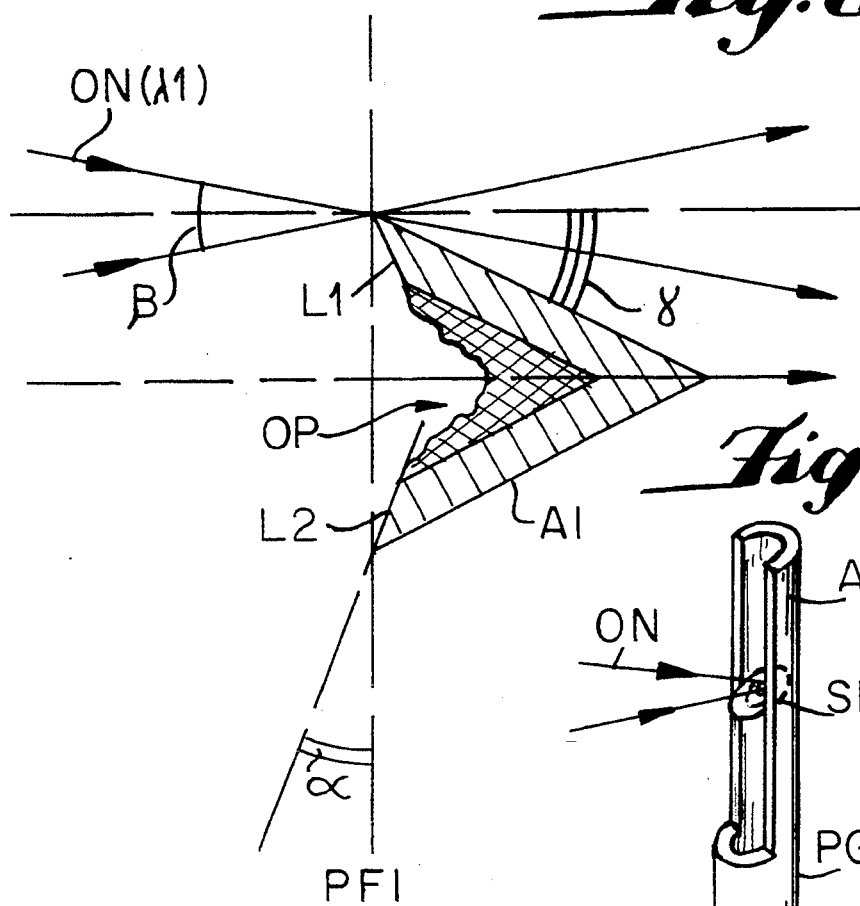
FIG. 8 schematically shows a needle of semirectangular cross section.

In a variant (FIG. 8), the absorption light trap includes a needle of triangular cross section cut longitudinally. The hollow part of the dihedral cross section forming the needle is opaque and has a predetermined width.

The needle A1 may contain a radiation microdetector (not shown) of the photodiode, photovoltaic or photoresistance type, capable of assuring both the absorption and the measurement of intensity of the radiation at the selected wavelength $\lambda 0$.

Figure 9:
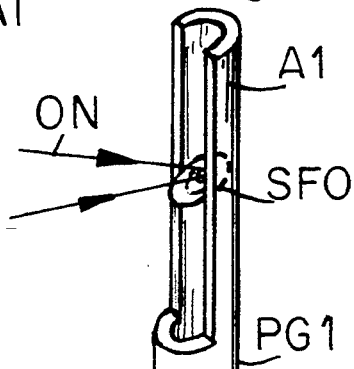
FIG. 9 schematically shows an optical fiber accommodated in a needle.

In another variant (FIG. 9), flux transmission at $\lambda 0$ can be transmitted or assured by an optical fiber FO to a detector (not shown), thanks to either a reversing microprism or an inclined section of the end of the fiber.

In that case, the optical fiber FO is accommodated in the tubular needle. The electromagnetic radiation ON at $\lambda 0$ then drops onto the surface of the end of the optical fiber SFO in order to be sent then along the optical fiber to a detector (not shown).

It should be noted that the passband FZ of the light trap is limited to the range of frequencies less than $\lambda 1$ and greater than $\lambda 2$ by the extreme edges of the means acting as an absorption light trap PG1.

It should also be noted that the beveled edges or lips L1 and L2 (FIGS. 7B and 8) of the means forming an absorption light trap may have a reflection other than 0.

To prevent such a reflection of the energy to the preceding dispersive stage, the angle $\alpha$ that the front face of the light trap forms with the focal plane PF1 must be larger than $\beta/2$, where $\beta$ is the flare angle of the beam to be analyzed through the transfer means M2.

On the other hand, to prevent the partial blacking out of the beam transmitted, the angle $\gamma$ that the back face of the light trap forms with the focal plane PF1 must also be greater than $\beta/2$.

Advantageously, the width of the absorption light trap means is variable.

Figure 10:
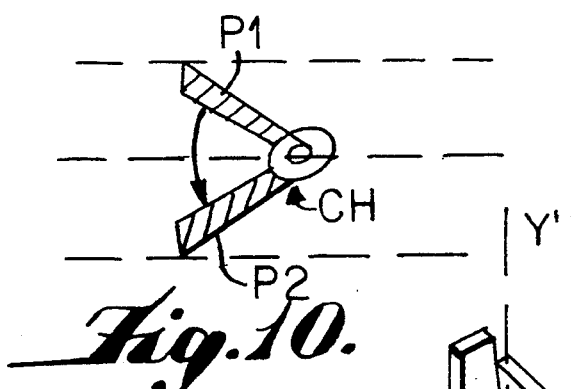
FIG. 10 illustrates a first embodiment of a variable-width absorption-type light trap.

FIG. 10 shows one way of varying the width of the absorption-type light trap means. For example, two plates P1 and P2 are articulated around a rotationally movable hinge CH, which enables varying the angle that the two plates P1 and P2 form.

Figure 11:
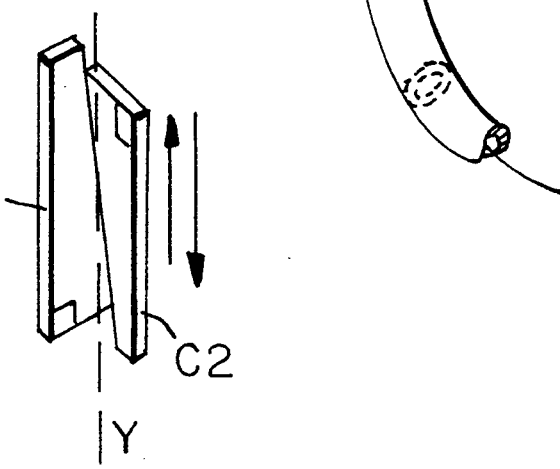
FIG. 11 illustrates a second embodiment of a variable-width absorption-type light trap.

In FIG. 11, two right-angled corners C1 and C2 are shown, whose hypotenuses are capable of sliding relative to an axis YY'.

Figure 12A:
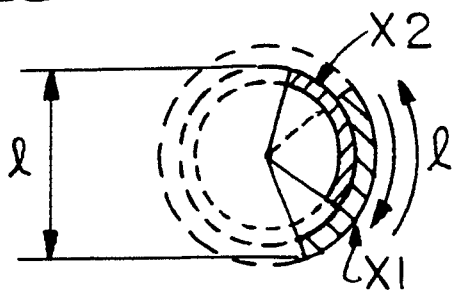
FIGS. 12A, 12B and 12C illustrates a third embodiment of a variable-width absorption-type light trap.
Figure 12B:
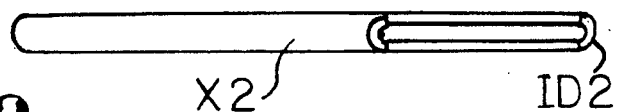
Figure 12C:
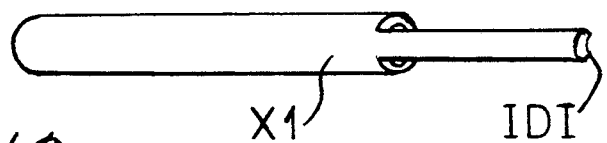

FIGS. 12A, 12B and 12C show means forming an absorption-type light trap, including a semicylindrical cover, with two coaxial parts X1 and X2 that are movable in rotation. For example, the two coaxial parts X1 and X2 are made with two coaxial tubes machined at the end and with different diameters ID1 and ID2.

According to the invention, the filtration means filter by transmission.

For example (FIG. 13), the transmission light trap is constituted by a transparent interval T1 between two lips of predetermined width 1T1, allowing a spectral band BZ of a predetermined spectral width to pass and centered on a selected frequency corresponding to the wavelength $\lambda 0$ of the electromagnetic radiation to be trapped.

The space or interval T1 is interposed between reflective surfaces T2 and T3 that are capable of reflecting the dispersed spectral image FZ, minus the aforementioned thus-trapped spectral band BZ, for the sake of a later analysis.

In practice, the second and third reflective surfaces T2 and T3 are rectilinear or curvilinear beveled edges, which makes it possible to defined a slot of predetermined width corresponding to the width 1T1 of the first transparent surface T1.

The spacing between the surfaces T1 and T2 makes it possible to vary the band 1T1.

According to the invention, the filtration means may also filter by reflection.

In that case (FIG. 14), the light trap includes a first reflective surface RTR1 of predetermined width R reflecting the spectral band BZ of a predetermined spectral width and centered on the aforementioned selected frequency corresponding to the wavelength of the electromagnetic radiation to be trapped.

The first reflective surface RTR1 is then interposed between the second and third transparent surfaces RTR2 and RTR3, to allow the dispersed spectral image FZ, minus the thus-trapped spectral band BZ, to pass through.

Advantageously, the transparent surfaces RTR2 and RTR3 are coated with an antireflective multidielectric layer on both faces.

For example, the surfaces RTR1, RTR2 and RTR3 are made on a slab L of transparent optical material, on which the aforementioned surfaces are defined.

It has been noted that the slab L (FIG. 15) must be inclined by an angle Z relative to the optical axis, in order that the reflection of the spectral band BZ will not return to the preceding dispersive stage, in this case R1, to prevent parasitic diffusion.

Figure 13:
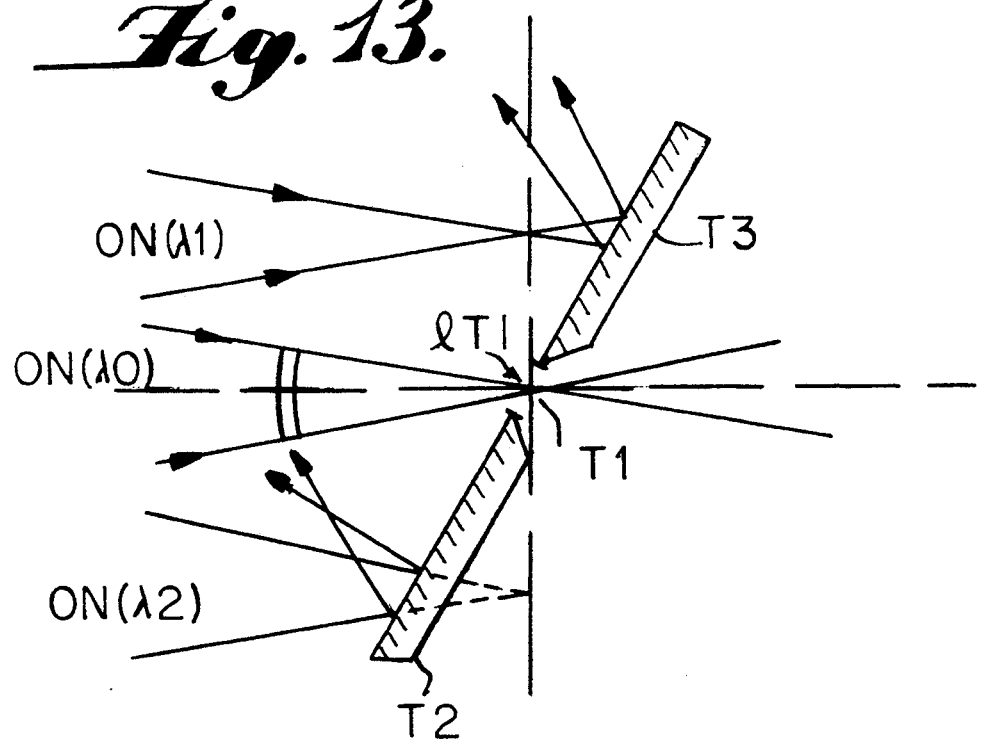
FIG. 13 is a schematic view of a transmission-type light trap according to the invention.
Figure 14:
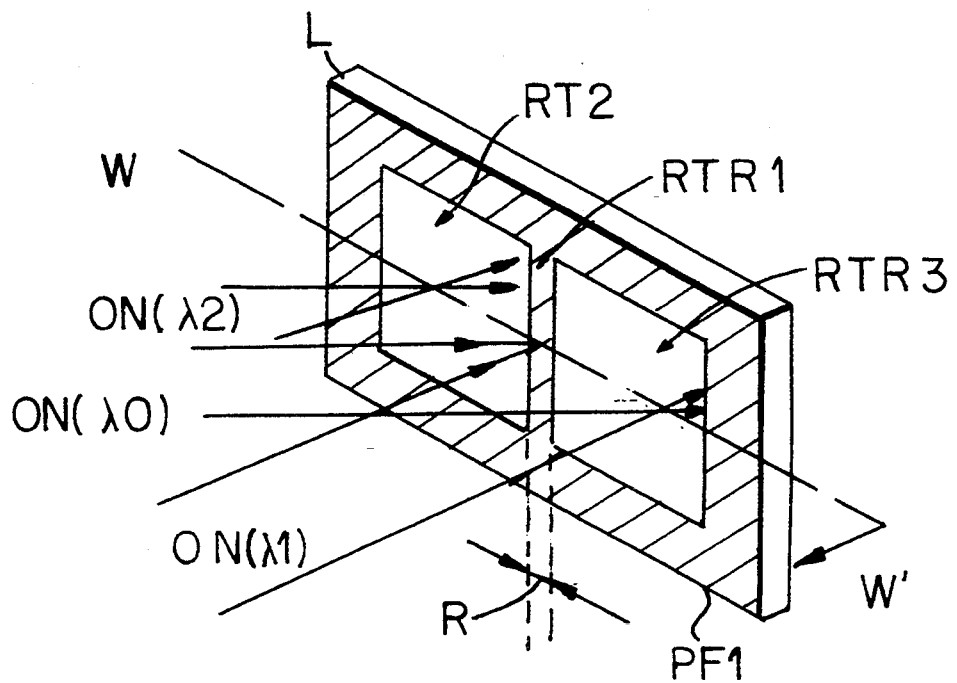
FIG. 14 is a schematic view of a reflection-type light trap according to the invention.
Figure 15:
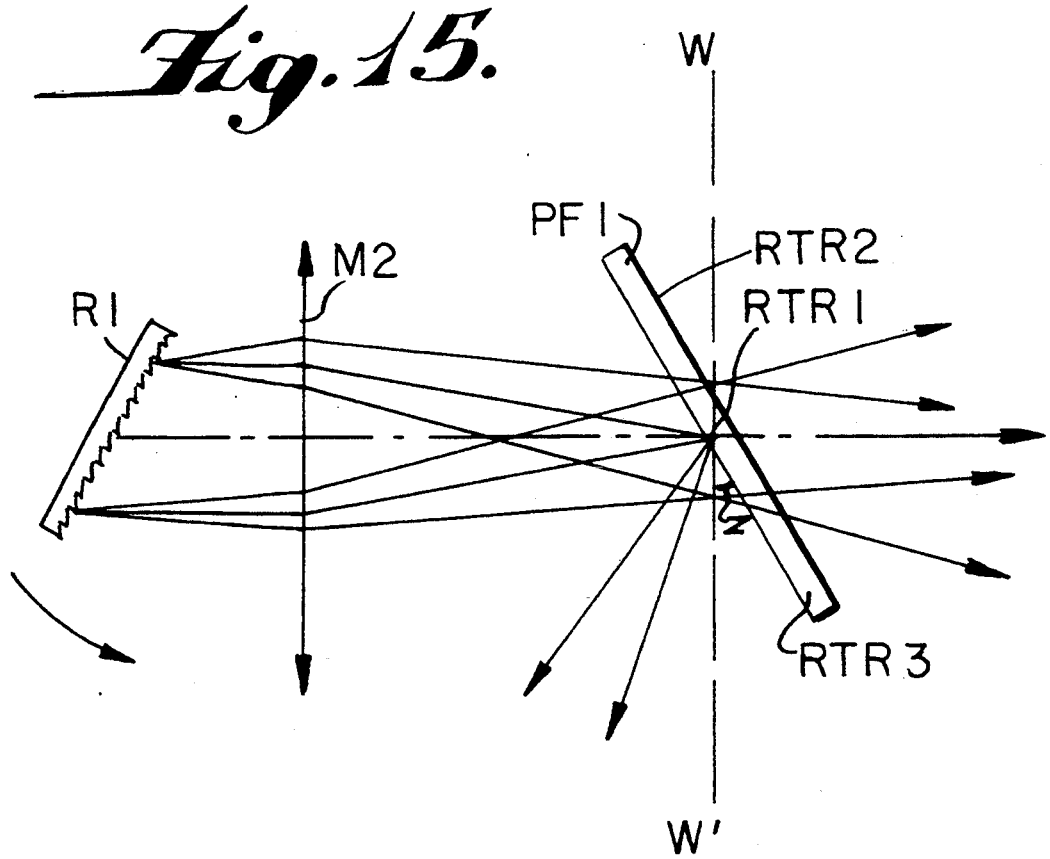
FIG. 15 is a sectional view taken along the line WW' through the light trap of FIG. 14 according to the invention.

The present application has surprisingly discovered that the transmission or reflection light trap as described in conjunction with FIGS. 13–15 can serve not only to reject a spectral band BZ of width l centered on $\lambda 0$, but also to inject this same spectral band BZ in the opposite direction into a dispersive spectrometry apparatus, on the one hand, or to assure both roles simultaneously, on the other.

The reflection- or transmission-type light trap then becomes a filter with at least two paths characterized by complementary spectral responses.

Such a filter, with at least two paths, finds a preferential but limiting application in Raman-scattering or fluorescence-type dispersive spectrometry installations.

Figure 16:
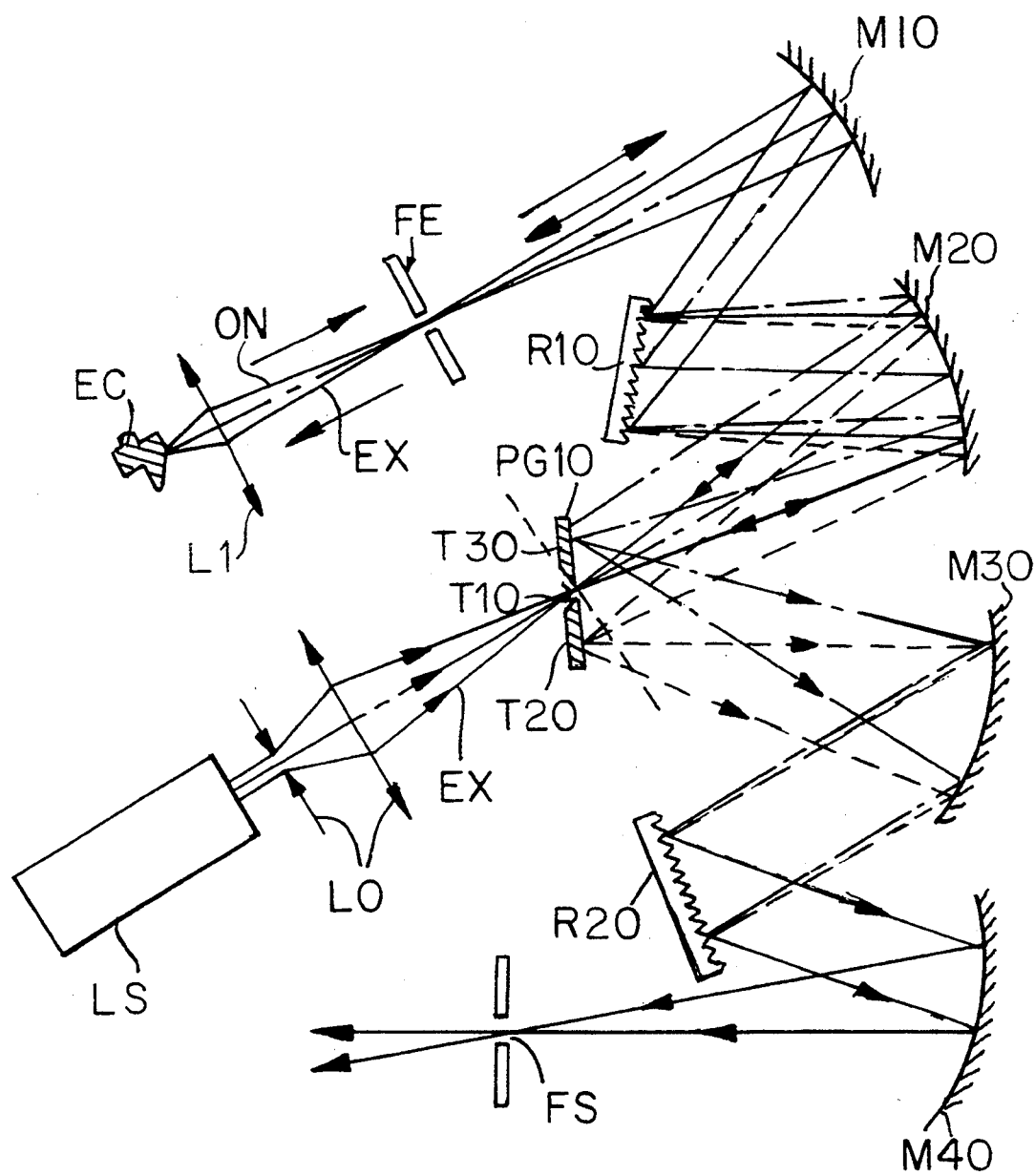
FIG. 16 is a schematic view of a dispersive spectrometry installation in which a transmission-type light trap serves both to inject the exciter ray and to reject it, according to the invention.

In FIG. 16, a premonochromator of the subtracting type, equipped with a transmission-type light trap according to the invention, has been shown, which performs the injection of the exciting radiation at λ0 in the first stage and the rejection of this exciting radiation in the second dispersive stage.

A monochromatic light source LS generates an exciting radiation EX with a wavelength λ0.

Advantageously a transmission-type light trap PG10 identical to that described in conjunction with FIG. 13, will transmit this exciting radiation EX at λ0 to a first dispersive stage R10.

More precisely, optical means LO focus the exciting radiation EX at λ0 onto the transmission surface T10 of the transmission-type light trap PG10. The optical means LO here constitute a beam expander, which adapts the flare angle of the beam EX to assure an optimal spatial resolution at the level of the specimen EC to be analyzed, In practice, the first dispersive stage includes the specimen EC to be analyzed, a lens, such as a microscope objective L1, for example, an inlet slit FE receiving the electromagnetic radiation ON to be analyzed, a collimator mirror M10, a dispersive network R10, and a mirror M20, forming a dispersed spectral image at the means forming a light trap PG10.

In the forward direction of the optical path, the exciting radiation EX at λ0 thus traverses the transmission surface T10 to be injected through the first dispersive stage to the specimen EC, via the successive optical elements M20, R10, M10, FE, and L1.

The present applicant has discovered, surprisingly, that this apparatus also constitutes a monochromator, which also performs a filtration of the exciting radiation by eliminating the components located outside the spectral passband BZ (which finds an application, for example, in the elimination of the plasma rays emitted by a gas laser, or lateral modes of a diode laser).

In the return direction of the optical path, the polychromatic light making up the beam ON resulting from the illumination of the specimen EC by the exciting radiation EX at λ0 is routed through the light trap at PG10 to be filtered via the successive optical elements L1, FE, M10, R10 and M20.

More precisely, the spectral portion forming the passband FZ of the dispersed spectral image is reflected toward the mirror M30 by the reflective surfaces T20 and T30 of the light trap PG10, while the spectral band BZ centered on λ0 is cast back to the source LF by the transmission surface T10.

The spectral portion forming a passband FZ, accordingly minus the spectral band BZ, is finally routed to an analysis spectrograph via a network R20, a mirror M40, and an outlet slit FS.

To improve the rejection of the diffusion of the exciting radiation λ0 by the optical elements of the first dispersive stage, it is possible according to the invention to connect in series a plurality of light traps like those described in conjunction with FIG. 16 and optically coupled as described in conjunction with FIG. 5.

In practice, the spectral response of the various light traps thus connected in series is centered on λ0.

In a variant, it is possible according to the invention to connection in series a plurality of light traps with different and noncomplementary spectral responses, centered on λa, λb, λc, etc., respectively.

With this variant, it is thus possible to achieve either the injection or the rejection of a plurality of excitation rays of different wavelengths, or the measurement of intensity of a plurality of rays selected within the spectrum.

Such a structure finds an application in thermal processing, photochemical processing, annealing, or laser ablation.

In another variant, it is possible according to the invention to provide a plurality of light traps that work by reflection, transmission or refraction, each making it possible to filter a plurality of narrow bands centered on different wavelengths.

Filtration means that according to the invention assure the injection of a first spectral band in a first optical direction and the rejection of this first spectral band in a second optical direction that is the reverse of the first can be used in other assemblies than that described in conjunction with FIG. 16.

Figure 17:
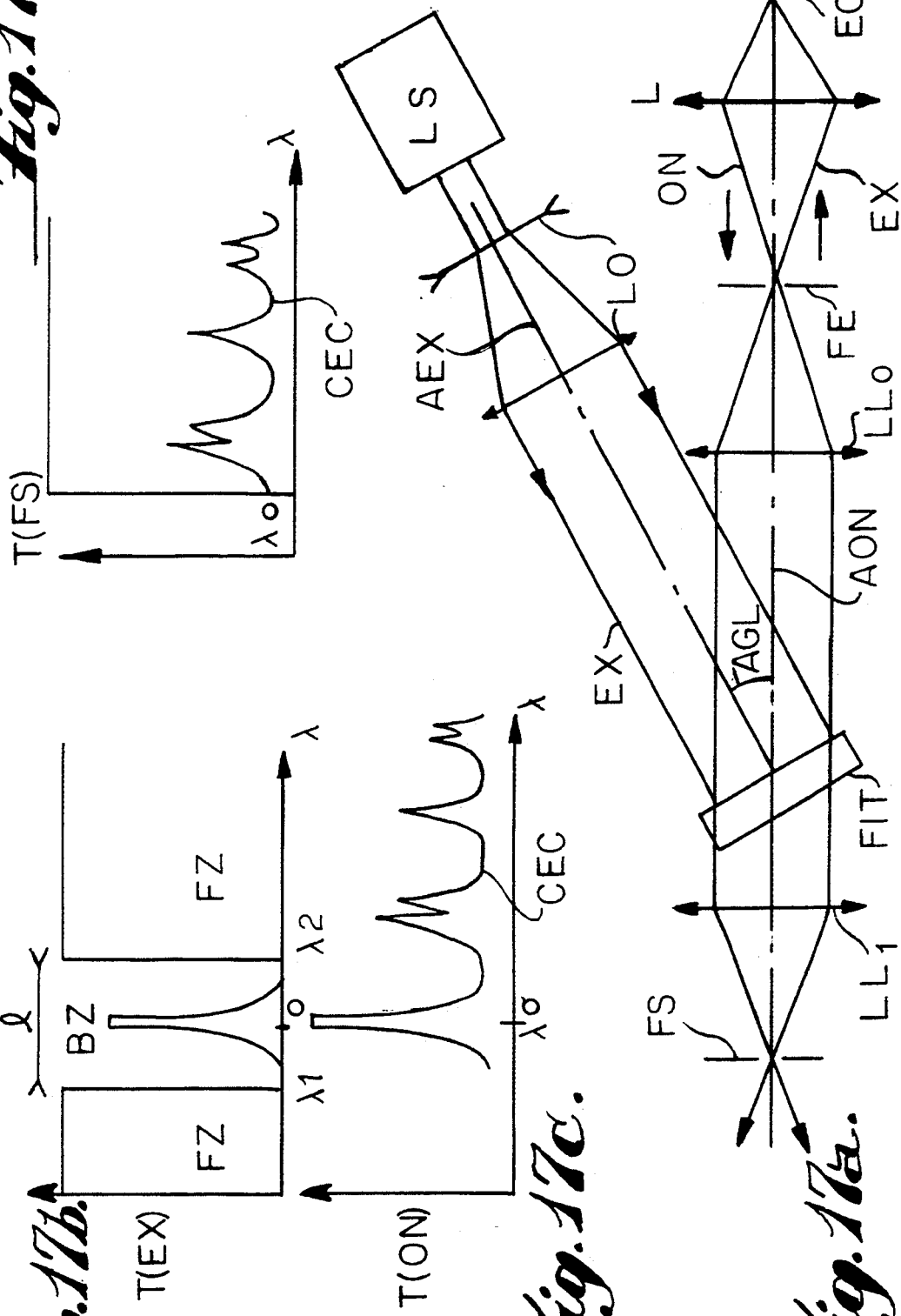
FIGS. 17A, 17B, 17C and 17D schematically represent a spectrometry installation equipped with nondispersive filtration means, according to the invention.

For example, FIG. 17A shows the essential elements of a spectrometric filtration apparatus lacking a dispersive stage.

It includes the generator means LS arranged to generate an exciter electromagnetic radiation EX of a predetermined wavelength λ0 along an excitation axis AEX; the specimen EC to be analyzed; and the inlet FE for the characteristic electromagnetic radiation beam ON to be analyzed of the specimen, along an analysis axis AON.

Advantageously, a beam expander including a diverging lens and a converging lens is disposed at the output of the generator means LS, to adapt the flare angle of the beam EX in order to assure an optimal spatial resolution at the level of the specimen EC to be analyzed.

According to the invention, filtration means FIT are placed in a predetermined geometric relationship with respect to the generator means LS.

In practice, the axis of the analysis beam, AON and the axis of the exciter beam AEX intersect at a predetermined intersection point PIN, while the aforementioned filtration means FIT are placed at the level of this intersection point PIN.

In other words, the axis of the beam to be analyzed, AON, and the axis of the exciter beam, AEX, form an angle AGL.

A lens such as a microscope objective L1, for example, an inlet slit FE receiving the electromagnetic radiation ON to be analyzed, and a lens LL0 are disposed on the optical path along the analysis axis AON on the right of the filtration means FIT in accordance with FIG. 17A.

In addition, a lens LL1 conjugated with the lens LL0 and an outlet slit FS are disposed along the analysis axis AON on the left of the filtration means FIT in accordance with FIG. 17A.

According to the invention, the filtration means FIT filter the exciter electromagnetic radiation EX in a first forward direction from the generator means LS to the specimen EC, by allowing a second spectral band BZ of predetermined spectral width l and centered on a selected frequency corresponding to the wavelength of the exciter radiation, λ0, to pass through, and stopping the first spectral band FZ which is complementary to the second spectral band BZ (FIG. 17B).

As a result, the beam ON to be analyzed, resulting from the illumination of the specimen EC by the exciter ray EX, thus filtered of its undesirable rays, now has a spectrum (FIG. 17C) including characteristic information CEC on the specimen to be analyzed and the exciter ray EX thus filtered.

Substantially simultaneously with this first filtration operation, the filtration means FIT also filter the electromagnetic radiation ON to be analyzed in a second direction that is the reverse of the first, by allowing the first spectral band FZ (that is, the information CEC) to pass through and stopping the second spectral and BZ (that is, the exciter ray EX) (FIG. 17D).

As mentioned above, such an assembly accordingly makes it possible to inject the exciter electromagnetic radiation EX into the optical means along an optical path that coincides with the analysis path ON, in the opposite direction and with the same flare angle of the beam.

In practice, the filtration means FIT are of the holographic type, of the kind sold by Kaiser Optical System (United States), opto-acoustical, interferometric, such as those of the Fabry Perot type, or a combination of these types.

Figure 18:
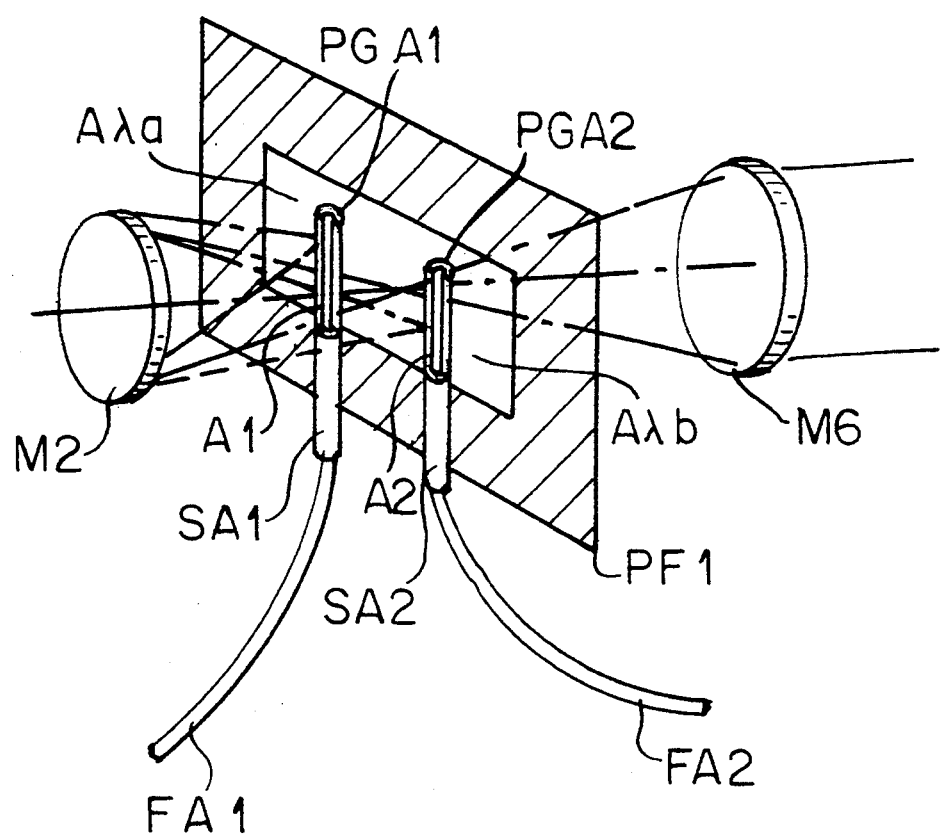
FIG. 18 is a schematic view of a double absorption-type light trap.

As shown in FIG. 18, two absorption-type light traps PGA1, PGA2 are provided, which are identical to that described in conjunction with FIG. 6.

The means M2 are seen, capable of forming the spectral image dispersed by the dispersive stage in a focal plane PF1, for selected wavelengths $\lambda a$, $\lambda b$.

Advantageously, the light traps PGA1 and PGA2 each include a respective needle A1 and A2 of cylindrical section cut longitudinally, mounted on a needle support SA1 and SA2, respectively, which is movable in a three-dimensional reference system.

In practice, the hollow portion of the semicylindrical section of the needles A1 and A2 is opaque and has a predetermined width.

Preferably, the optical fibers FA1 and FA2 are accommodated in the needles A1 and A2, respectively, for carrying the luminous fluxes thus received via the needles A1 and A2.

Because of the needle supports that are movable in a three-dimensional reference system, it is possible to adjust the intersection points A$\lambda a$ and A$\lambda b$ of the spectral image with the focal plane PF1 for the wavelengths $\lambda a$ and $\lambda b$.

Figures 19, 20:
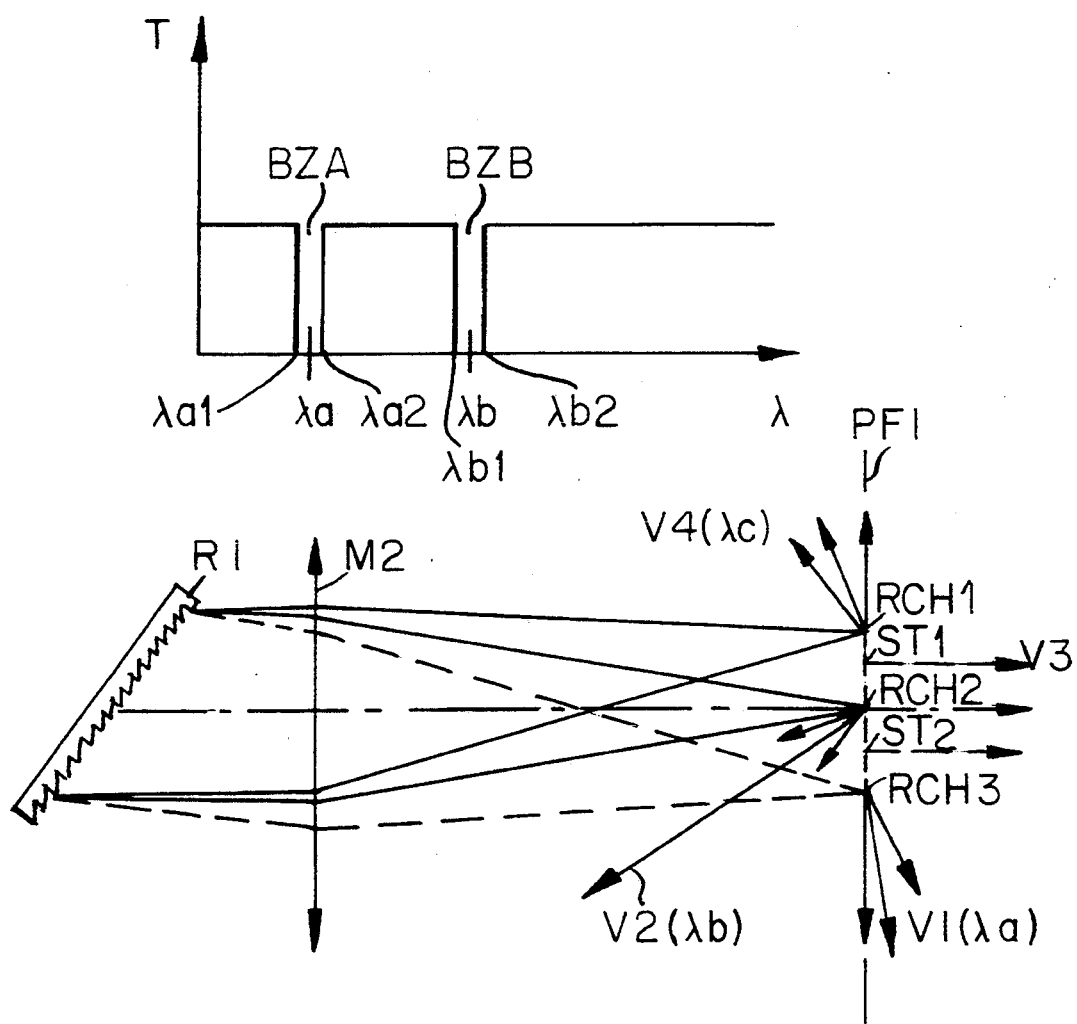
FIG. 19 shows the spectral response of the light trap of FIG. 18.
FIG. 20 is a sectional view through a triple reflection-type light trap according to the invention.

In FIG. 19, the spectral response of the two light traps PGA1 and PGA2 of FIG. 18 has been shown.

This double light trap allows the radiation having a wavelength less than $\lambda a1$ and a wavelength greater than $\lambda a2$, as well as radiation having a wavelength less than b1 and a wavelength greater $\lambda b2$, to pass with an elevated transmission value.

Conversely, the double light trap eliminates, with a zero transmission value, the radiation having a wavelength between $\lambda a1$ and $\lambda a2$ and centered on $\lambda a$, as well as the radiation having a wavelength between $\lambda b1$ and $\lambda b2$ and centered on $\lambda b$.

In practice, the eliminated or rejected spectral bands BZ1 and BZ2 have widths that are proportional to the difference $\lambda a2 - \lambda a1$ and $\lambda b2 - \lambda b1$.

A triple light trap operating by reflection is shown im FIG. 20.

This shows the dispersive network R1 which delivers a dispersed spectral image, transferred by the mirror M2, to the focal plane PF1.

The triple reflection-type light trap includes three reflective screens RCH1, RCH2 and RCH3, spaced apart from one another by two transparent surfaces ST1, ST2.

The screens RCH1, RCH2 and RCH3 constitute four filtration paths for three different wavelengths $\lambda a$, $\lambda b$ and $\lambda c$.

The first filtration path V1 is embodied by the reflective screen RCH3, which reflects the radiation at $\lambda a$.

The second filtration path V2 is embodied by the reflective screen RCH2, which reflects the radiation at $\lambda b$.

The third filtration path V3 is embodied by the transparent surfaces ST1 and ST2, which allow the radiation different from $\lambda a$, $\lambda b$ and $\lambda c$ to pass through.

The fourth filtration path V4 is embodied by the reflective screen RCH1, which reflects the radiation $\lambda c$.

Figure 21:
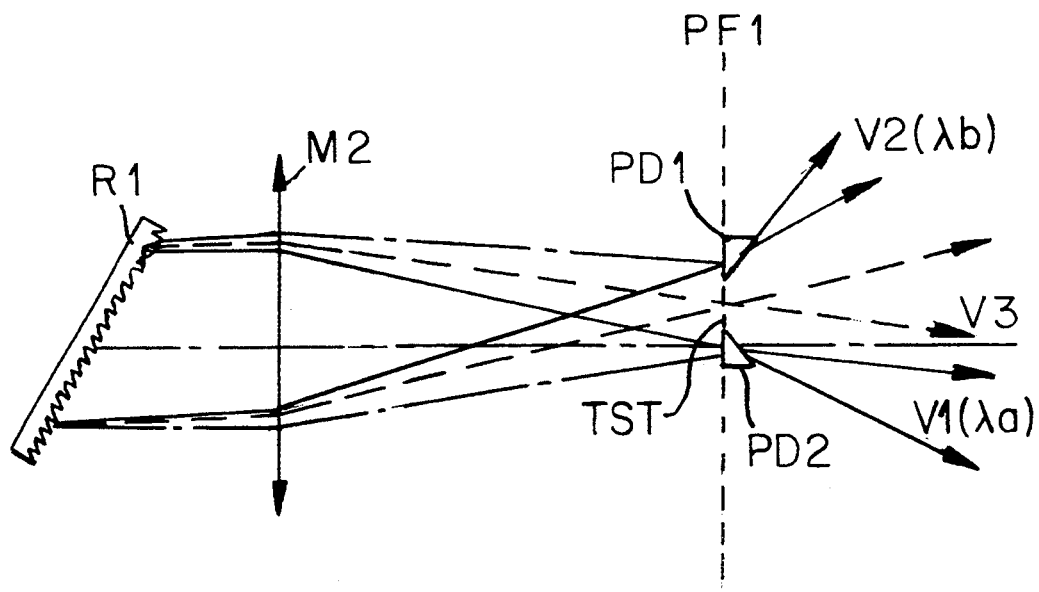
FIG. 21 is a sectional view through a double refraction-type light trap according to the invention.

A double refraction-type light trap has been shown in FIG. 21.

It includes the dispersive network R1, which delivers a dispersed spectral image transferred via the mirror M2 to the focal plane PF1.

The double reflection-type light trap includes two deviator prisms PD1 and PD2, spaced apart from one another by a transparent surface TST.

The deviator prisms PD1 and PD2 constitute two filtration paths.

The first filtration path V1 is embodied by the deviator prism PD1 which deviates the radiation at $\lambda a$.

The second filtration path V2 is embodied by the deviator prism PD2 which deviates the radiation at $\lambda b$.

The third filtration path V3 is embodied by the transparent surface TST, which allows the radiation different from $\lambda a$ and $\lambda b$ to pass through.

Figure 22:
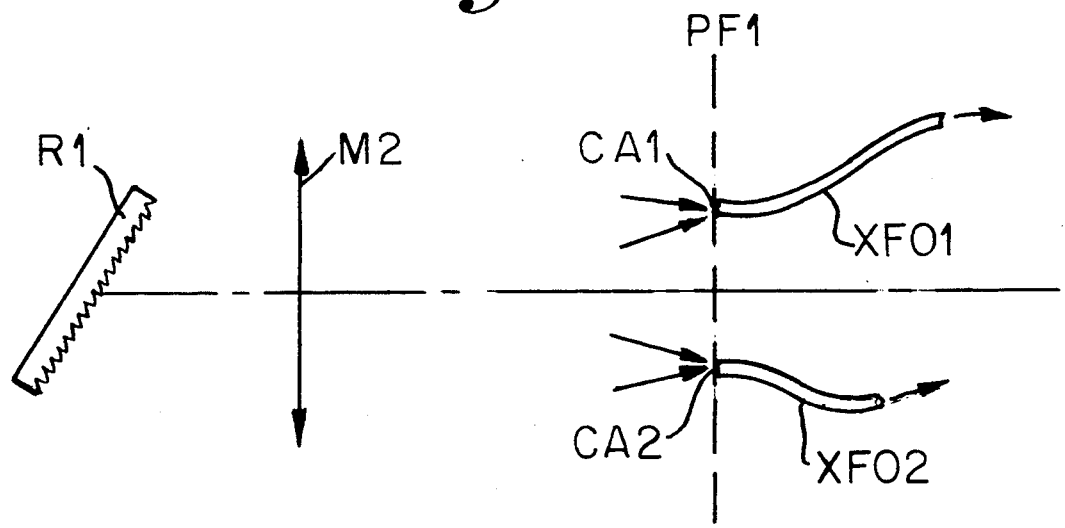
FIG. 22 is a sectional view through a double absorption-type light trap equipped with optical fibers.

A double absorption-type light trap is shown in FIG. 22.

The double light trap includes two absorbent screens CA1 and CA2, connected by optical fibers XF01 and XF02 to measurement means (not shown).

We claim:

1. A spectrometry apparatus comprising:
   a light source (LS) for generating an exciter electromagnetic radiation (EX);
   a location for a specimen (EC) for receiving the exciter electromagnetic radiation (EX) and producing a scattered light incorporating a desired Raman spectrum and stray light of the light source;
   at least one dispersive stage having an inlet (FE), near said location, for receiving the produced scattered light from said specimen, a dispersive element (R10) for receiving through said inlet the scattered light in order to filter the stray light and to select the desired Raman spectrum (FZ) and transfer means (M10,M20) positioned opposite said element (R10) for forming a spectral image of said desired Raman spectrum, dispersed by the dispersive element (R10), in a predetermined focal plane;
   filtration means (PG10), by transmission/reflection positioned at said predetermined focal plane, and arranged for filtering at least a first filtration operation by admitting the exciter radiation (EX) in a first forward direction from the light source (LS) to the specimen via the one dispersive stage (R10) and while substantially simultaneously with said first filtration operation, said filtration means further filtering the spectral image of the desired Raman spectrum in a second direction that is reverse of the first direction, by transmitting light at the exciter radiation wavelength, and by reflecting off the spectral image of the desired Raman spectrum (FZ) thus filtered.

2. The apparatus of claim 1, characterized in that the filtration means are removable.

3. The apparatus of claim 1, characterized in that the filtration means are movable in a three-dimensional reference system.

4. The apparatus of claim 1, characterized in that the filtration means include a first transparent surface (T10) and at least a second reflective surface (T20 or T30), the first transparent surface having the property of passing the exciter radiation within a narrow band of wavelengths (BZ) and the second reflective surface having the property of reflecting the remaining light of other wavelengths (FZ).

5. The apparatus of claim 4, characterized in that the at least second reflective surface has rectilinear or curvilinear beveled edges, which enables the definition of a slit of predetermined width corresponding to the width of the first transparent surface.

6. The apparatus of claim 1, characterized in that said filtration means include a plurality of filtration means, whose spectral responses are centered on a selected wavelength ($\lambda 0$).

7. The apparatus of claim 1 further comprising a second dispersive element (R20) for receiving the spectral image of the desired Raman spectrum (FZ) reflected off by the filtration means (PG10), second transfer means (M30, M40) positioned opposite said second dispersive element (R20) for forming a second spectral image, with null dispersion, in a second focal plane, and a outlet (FS) positioned at said second focal plane.

8. A spectrometry apparatus comprising:
a light source (LS) for generating an exciter electromagnetic radiation (EX);
a location for a specimen (EC) for receiving the exciter electromagnetic radiation (EX) and producing a scattered light incorporating a desired Raman spectrum and stray light of the light source;
at least one dispersive stage having an inlet (FE), positioned near said location for receiving the produced scattered light from said specimen, a dispersive element (R10) for receiving through said inlet the scattered light in order to filter the stray light and to select the desired Raman spectrum (FZ) and transfer means (M10,M20) positioned opposite said dispersive element (R10) for forming a spectral image of said desired Raman spectrum, dispersed by the dispersive element (R10), in a predetermined focal plane;
filtration means (PG10), by transmission/reflection positioned at said predetermined focal plane, and arranged for filtering at least a first filtration operation by admitting the exciter radiation (EX) in a first foward direction from the light source (LS) to the specimen via the one dispersive stage (Ri0), and while substantially simultaneously with said first filtration operation, said filtration means filtering the spectral image of the desired Raman spectrum in a second direction that is reverse of the first direction, whereby the filtration means comprise a first reflective surface of predetermined width reflecting the excitation radiation, said first reflective surface being interposed between second and third transparent surface for allowing the Raman spectrum to pass.

9. The apparatus of claim 8, characterized in that said filtration means include a plurality of filtration means whose spectral responses are centered respectively on different wavelengths ($\lambda a, \lambda b, \lambda c$).

* * * * *